United States Patent
Neddermeier

(10) Patent No.: US 10,241,029 B2
(45) Date of Patent: Mar. 26, 2019

(54) METHOD OF EXPANDING THE MEASUREMENT RANGE OF PHOTOMETRIC SYSTEMS

(71) Applicant: GEBRÜDER HEYL ANALYSENTECHNIK GMBH & CO. KG, Hildesheim (DE)

(72) Inventor: Rüdiger Neddermeier, Hildesheim (DE)

(73) Assignee: GEBRÜDER HEYL ANALYSENTECHNIK GMBH & CO. KG (DE)

( * ) Notice: Subject to any disclaimer, the term of this patent is extended or adjusted under 35 U.S.C. 154(b) by 70 days.

(21) Appl. No.: 15/108,732

(22) PCT Filed: Feb. 12, 2015

(86) PCT No.: PCT/EP2015/000312
§ 371 (c)(1),
(2) Date: Feb. 22, 2017

(87) PCT Pub. No.: WO2015/165559
PCT Pub. Date: Nov. 5, 2015

(65) Prior Publication Data
US 2017/0167971 A1    Jun. 15, 2017

(30) Foreign Application Priority Data
Apr. 30, 2014   (DE) .................. 10 2014 006 317

(51) Int. Cl.
*G01N 21/00*   (2006.01)
*G01N 21/25*   (2006.01)
(Continued)

(52) U.S. Cl.
CPC ............. *G01N 21/25* (2013.01); *G01N 21/79* (2013.01); *G01N 21/85* (2013.01); *G01N 31/16* (2013.01)

(58) Field of Classification Search
CPC .... B01L 9/54; B01L 3/502; B01L 2300/0825; B01L 3/5082; B01L 3/5085; A61B 5/097;
(Continued)

(56) References Cited

U.S. PATENT DOCUMENTS

| | | | |
|---|---|---|---|
| 3,932,131 A | 1/1976 | Rolfo-Fontana | |
| 2005/0276724 A1* | 12/2005 | Bremauer | B01F 15/0217 422/29 |

FOREIGN PATENT DOCUMENTS

| | | |
|---|---|---|
| CN | 1359005 | 7/2002 |
| CN | 101484795 | 7/2009 |

(Continued)

OTHER PUBLICATIONS

ISA / EP, International Search Report and Written Opinion prepared for PCT/EP2015/000312, dated Jun. 1, 2015.

*Primary Examiner* — Dennis White
(74) *Attorney, Agent, or Firm* — McDonald Hopkins LLC

(57) ABSTRACT

The present invention relates to a method of extending the measurement range during the determination of the concentration of a dissolved substance (2), where the solution of the dissolved substance (2) is metered by means of a micrometering device (3, 4, 5) to a specified amount of precharged reagent (1) into a measuring cell (11) until the coloration which forms as a result of the reaction of the dissolved substance with the reagent, ascertained photometrically, achieves a predetermined extinction value X, whereupon the amount of consumed dissolved substance (2) is ascertained (Continued)

at the micrometering device (3, 4, 5) and the concentration is calculated on the basis of this, where the volume of (2) is much smaller than of (1).

4 Claims, 1 Drawing Sheet

(51) Int. Cl.
*G01N 31/16* (2006.01)
*G01N 21/79* (2006.01)
*G01N 21/85* (2006.01)

(58) Field of Classification Search
CPC . A61B 10/00; A61B 5/082; A61B 2010/0087; A61B 2560/0443; A61B 2562/0276; A61B 2562/0285; A61B 5/083; G01N 33/98; G01N 33/4972
See application file for complete search history.

(56) References Cited

FOREIGN PATENT DOCUMENTS

| CN | 101706442 | 8/2011 |
|---|---|---|
| EP | 1506813 A1 | 2/2005 |
| TW | 200506363 | 2/2005 |
| WO | 95/03537 A1 | 2/1995 |
| WO | 2009/017461 A1 | 2/2009 |

* cited by examiner

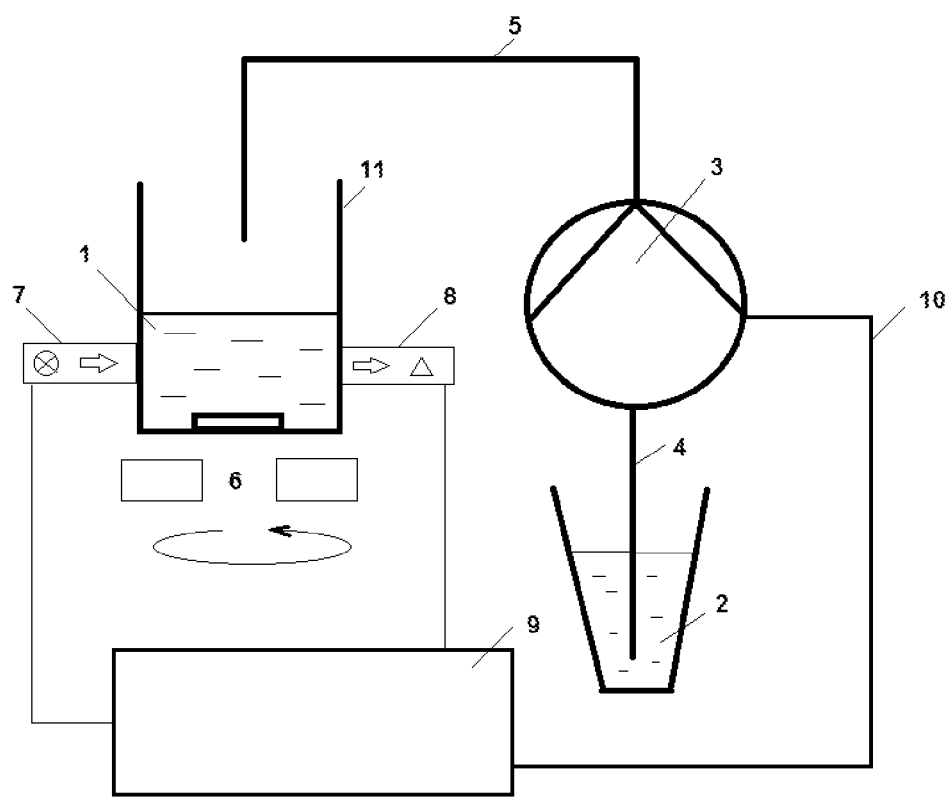

METHOD OF EXPANDING THE MEASUREMENT RANGE OF PHOTOMETRIC SYSTEMS

CROSS-REFERENCE TO RELATED APPLICATIONS

This application is a 35 U.S.C. 371 national stage filing and claims priority to PCT Application No. PCT/EP2015/000312 entitled "METHOD FOR EXPANDING THE MEASUREMENT RANGE OF PHOTOMETRIC SYSTEMS," filed Feb. 12, 2015, which claims the benefit of German Application No. 10 2014 006 317.8 filed Apr. 30, 2014, each of which is incorporated by reference herein in its entirety.

FIELD

The present invention relates to a method of extending the measurement range of photometric systems. In particular, the invention relates to a photometric method for determining relatively high concentrations. Furthermore, the present invention relates to a method for determining the chlorine content in fluids.

BACKGROUND

Photometric measurements are used inter alia for determining concentration. If light is passed through the solution of an absorbing substance, then the intensity of the transmitted proportion is dependent, according to the Beer-Lambert law, on the material properties of the substance, the concentration and the path length through which the light passes.

$$E = \varepsilon * c * d$$

E=extinction (logarithm of the quotient of the intensity of the incident and transmitted light proportion)
$\varepsilon$=extinction coefficient (substance-specific)
c=concentration of the substance
d=path length of the solution through which the light passes Concentration determinations are usually carried out by mathematically ascertaining the ratio of known substance concentrations c to their extinction E and thus being able to calculate unknown concentrations by reference to extinction measurements. This means in practice often: for the photometric measurement, a specified volume of the reagent causing a coloration with the substance to be determined is combined with a specified volume of a solution of the substance of unknown concentration and mixed and the extinction E (absorption) of the resulting coloration is measured photometrically in a vessel with specified dimensions (measuring cell with path length d), where the unknown concentration of the sample is ascertained by reference to the extinction value by comparison with calibration values of known concentrations.

The substance-specific extinction coefficient $\varepsilon$ is often configured for customary photometric measurement methods in such a way that only samples with a relatively low concentration c can be measured. This means the realizable measurement ranges of this method are limited on the part of the applicability of the Beer-Lambert law, the substance-specific properties, and the apparatus possibilities of the measurement systems used. An extension of the measurement range is usually realized through a dilution of the substance preceding the actual measurement or a reduction in the path length d.

EP 1 825 915 A2 relates to a handheld device for metering and optionally titrating. A piston, moved by step motors, drives sample fluid into a vessel where the other part of the titration partner is located. A color change is ascertained with a sensor and controls the step motor of the handheld device in order to find the change point with higher accuracy. The document does not report anything about using samples with high concentrations.

SUMMARY

An object of the present invention is therefore to provide a photometric method for determining substances which are present in high concentration, where no preceding dilution of the sample is required.

BRIEF DESCRIPTION OF THE DRAWINGS

FIG. 1 shows an example of a measuring device according to the invention.

DETAILED DESCRIPTION

Surprisingly, it has been found that the stepwise introduction of a sample solution with a relatively high substance concentration (e.g. around 2 g/l in the case of the determination of chlorine in aqueous solution) via a micrometering device, preferably a micrometering pump, to a solution of a reagent located in a measuring cell in the case of the chlorine determination with an N,N-diethyl-p-phenylenediamine sulfate solution (DPD) until, by photometric means, with the extinction coefficient $\varepsilon$ (9800 $l*mol^{-1}*cm^{-1}$) a certain extinction is reached and ascertainment of the consumed sample solution permits the determination of a considerably higher concentration than the maximum normally permitted (in the case of customary chlorine determination 5 mg/l).

The aforementioned object is achieved by a method for extending the measurement range during the photometric determination of the concentration of a dissolved substance or sample 2, where the solution of the dissolved substance 2 is metered by means of a micrometering device 3, 4, 5 to a specified amount of precharged reagent 1 into a measuring cell 11 until the coloration which forms as a result of the reaction of the dissolved substance with the reagent, ascertained photometrically, achieves an extinction value X, corresponding to a known concentration of substance 2, whereupon the amount of consumed dissolved substance 2 is ascertained at the micrometering device 3, 4, 5 and the concentration is calculated as follows:

$$c_x = c_{known} * (V_1 + V_2)/V_2$$

where
$c_x$ is the concentration of the dissolved substance 2 to be determined,
$c_{known}$ is a known concentration of the dissolved substance 2,
$V_1$ is the volume of the measuring cell with the solution of reagent 1, and
$V_2$ is the volume of the solution of the dissolved substance 2 consumed with the micrometering device 3, 4, 5, and where $V_2 < V_1$.

Preferably, the volume ratio of $V_2$ to $V_1$ is in the range from 1:200000 to 1:10. More preferably, the volume ratio of $V_2$ to $V_1$ is in the range from 1:200000 to 1:100, preferably in the range from 1:200000 to 1:1000, in particular in the range from 1:200000 to 1:5000 or in the range from 1:200000 to 1:10000.

Preferably, the concentration ratio of $c_{known}$ to $c_x$ is in the range from 1:200000 to 1:10. More preferably, the concentration ratio of $c_{known}$ to $c_x$ is in the range from 1:200000 to 1:100, preferably in the range from 1:200000 to 1:1000, in particular in the range from 1:200000 to 1:5000 or in the range from 1:200000 to 1:10000.

Preferably, the known concentration of the dissolved substance is selected such that an extinction of 0.5 results. However, it is also possible to select any other extinction value provided the accuracy during the measurement still suffices and it is assigned to a certain known concentration $c_{known}$.

Further preferred embodiments are defined in the dependent claims.

FIG. 1 shows an example of a measuring device according to the invention.

The method is similar to the principle of an inverse titration and can be applied to any desired other customary photometric methods provided the reaction-kinetic conditions permit this. The principle of inverse titration, on which the present invention is based, can be found, for example, during the determination of nitrite according to Lunge. The titration is performed here by pouring the sample solution (nitrite solution) into the burette and slowly adding it dropwise to a $KMnO_4$ measurement solution as initial charge with heating of the latter until the coloration has disappeared. The motives for swapping the solutions with regard to a customary titration are, in contrast to the object of the present invention, exclusively of a reaction-kinetic nature.

The invention is illustrated below in more detail by reference to a chlorine determination. Chlorine solutions can be determined photometrically with regard to their chlorine concentration. In particular, aqueous chlorine solutions are used widely in industry and in water hygiene. Chlorine dissolves to about 7 g in 1 l of water. For sterilizing solutions in swimming pools, chlorine concentrations of 0.3 to 0.6 mg/l water are generally used.

Various measurement methods are customary. Among these, so-called photometric determination with N,N-diethyl-p-phenylenediamine reagent (DPD) has achieved great importance. Methods which use DPD as reagent for determining chlorine in water are described e.g. in GB 2,312,953 A or CN 103616373A. DPD reacts with chlorine-containing water to form a red coloration, meaning that the relatively low chlorine concentrations required for customary applications can be readily ascertained. DIN 38 408, Part 4-2 (replaced by EN ISO 7393-2 : 2000) prescribes the method for water analysis. The measurement parameter used is the absorption in the maximum of the UV/VIS spectrum of the red dye which is formed as result of the reaction of DPD with $Cl_2$. During the reaction of chlorine from the chlorine-containing aqueous sample with DPD, a colored radical, namely Wurster's red, is firstly formed if relatively small amounts of chlorine react with DPD. If the chlorine concentration increases, the conversion to the imine, which is colorless, takes place:

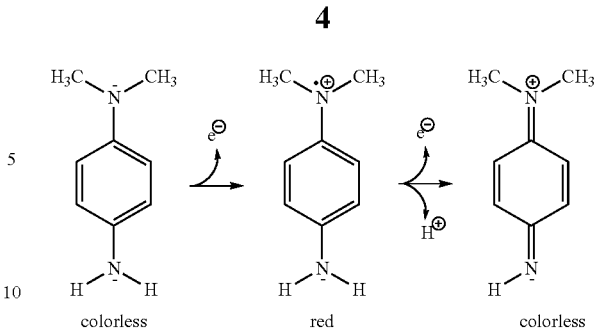

colorless    red    colorless

DPD is generally used as N,N-diethyl-p-phenylenediamine sulfate salt. In principle, however, other water-soluble salts of DPD are also suitable, provided they do not require an oxidation since the DPD base is oxidation-sensitive and even in air starts to react with the oxygen to form colored oxidation products.

The absorption of the red Wurster dye is proportional to the dye concentration present or to the available amount of free chlorine.

The method is highly suitable for chlorine concentrations in the range up to 5 mg/l, i.e. for the customary chlorine concentrations in treated water. Other halogen solutions as well as solutions of hypohalogenites can also be ascertained. In principle, it is possible to determine concentrations of solutions in which the substance to be determined has an oxidation potential that suffices for the formation of the Wurster dye. As well as applying to the aforementioned halogens and halogen compounds, this also applies e.g. to ozone or peroxides. The determination of higher concentrations becomes more difficult, e.g. chlorine concentrations up to, for example, 2 g/l. When using the process explained above, a preceding dilution step of about 1:1000 is required. For routine measurements, this is laborious and time-consuming. Consequently, the method according to the invention is used, which is explained below by way of example by reference to the chlorine determination with DPD.

In the case of the determination of chlorine in water at a concentration of approx. 2 g/l, the procedure is therefore as follows. For a measurement system, an optimum photometric working point is selected from the ratio of substance concentrations $c_{known}$ to their extinction E known for this system.

To a known volume $V_1$ of the reagent solution for the substance to be determined is added, by means of a high-resolution micrometering pump, a volume $V_2$ of the (highly concentrated) solution with the concentration $c_x$ of the substance to be determined until the pregiven photometric working point is reached (thus therefore the extinction for a concentration $c_{known}$ is reached).

The concentration $c_x$ of the highly concentrated solution can be calculated easily by reference to the equation $$c_x = c_{known} * (V_1 + V_2)/V_2.$$

The measurement range is therefore only still dependent on the ratio of the pregiven volume $V_1$ and on the resolution of the micrometering device.

The extinction X (absorption) of the coloration can preferably be measured photometrically at 500 to 560 nm. Preference is given to a wavelength of 510 nm (optimum of the extinction curve).

An example of a device used in the method according to the invention is equipped with a vessel for the sample 2, a measuring cell 11, a micrometering device 3, 4, 5,
a light source 7, preferably for monochromatic light,
a light receiver 8
a measuring and control unit 9 and
optionally a mixing device 6,
where the light receiver 8 and the micrometering device 3, 4, 5 are joined to the measuring and control unit 9 in a functional manner such that, after an extinction value X has been reached, the consumption of the micrometering device 3, 4, 5 is ascertained.

The sample solution can be in one area of the micrometering device, in which case feed line 4 is dispensed with. This applies for example to micrometering devices of the injection type with a piston pressurized by a step motor.

REFERENCE NUMERAL LIST

1 reagent solution
2 sample solution
3 micrometering device
4 feed line to the device
5 feed line to the measuring cell 11
6 mixing device—here magnetic stirring device
7 light emitter
8 light receiver
9 measuring and control unit and measurement value processing
10 signal line from 3 to 9 (to ascertain the metered amount of sample solution)
11 measuring cell

EXAMPLE (Chlorine Determination)

In accordance with the prior art, photometric chlorine determinations by means of the so-called DPD method are possible up to a maximum of 5 mg/l.

The absorption of a solution which comprises 2 mg/l of chlorine is approx. 0.5 (optimum working point).

A measuring cell 11 with a volume $V_1$=20 ml, and a micrometering pump 3, 5 with a volume store of 2 ml and a resolution of 0.2 µl (10000 steps per volume store) are used. 100 steps are metered from a highly concentrated chlorine solution 2.

$c_{known}$=2 mg/l
$V_1$=20 ml
$V_2$=100*0.2 µl=20 µl=0.02 ml
$c_x=c_{known}*(V_1+V_2)/V_2$
$c_x$=2 mg/l*(20 ml+0.02 ml)/0.02 ml
$c_x$=2002 mg/l In the present example, a measurement range extension from 5 mg/l to 2000 mg/l can thus be realized.

The invention claimed is:

1. A method of extending the measurement range during the photometric determination of the concentration of a dissolved substance, where the solution of the dissolved substance is metered by means of a micrometering device to a specified amount of precharged reagent into a measuring cell until the coloration which forms as a result of the reaction of the dissolved substance with the reagent, ascertained photometrically, achieves an extinction value X, corresponding to a known concentration of substance, whereupon the amount of consumed dissolved substance is ascertained at the micrometering device and the concentration is calculated as follows:

$$c_x=c_{known}*(V_1+V_2)/V_2$$

where
$c_x$ is the concentration of the dissolved substance to be determined,
$c_{known}$ is a known concentration of the dissolved substance,
$V_1$ is the volume of the measuring cell with the solution of reagent, and
$V_2$ is the volume of the solution of the dissolved substance consumed with the micrometering device, and
where $V_2<V_1$.

2. The method as claimed in claim 1, where the ratio of $V_2$ to $V_1$ is in the range from 1:200000 to 1:10.

3. The method as claimed in claim 1, where the dissolved substance to be determined is a solution of a halogen or a hypohalogenite and the reagent comprises a solution of N,N-diethyl-p-phenylenediamine (DPD).

4. The method as claimed in claim 3, where the dissolved substance is chlorine in aqueous solution.

* * * * *